(12) United States Patent
Setlur et al.

(10) Patent No.: US 8,910,507 B2
(45) Date of Patent: Dec. 16, 2014

(54) VARIABLE GAS SOURCE GAS EXCHANGE SYSTEM

(75) Inventors: Pradeep Setlur, Carmel, IN (US); Yang Yang, Zionsville, IN (US); Kirsti A. Golgotiu, Oregon City, OR (US)

(73) Assignee: Dow AgroScience, LLC., Indianapolis, IN (US)

( * ) Notice: Subject to any disclaimer, the term of this patent is extended or adjusted under 35 U.S.C. 154(b) by 372 days.

(21) Appl. No.: 13/534,374

(22) Filed: Jun. 27, 2012

(65) Prior Publication Data

US 2013/0008228 A1    Jan. 10, 2013

Related U.S. Application Data

(60) Provisional application No. 61/505,399, filed on Jul. 7, 2011.

(51) Int. Cl.
*G01N 33/497*    (2006.01)
*G01N 33/00*     (2006.01)

(52) U.S. Cl.
CPC .................................. *G01N 33/0009* (2013.01)
USPC ........................................... 73/23.2; 73/865.6

(58) Field of Classification Search
CPC .... G01N 1/26; G01N 1/2226; G01N 33/0098
USPC ................................................ 73/23.2, 865.6
See application file for complete search history.

(56) References Cited

U.S. PATENT DOCUMENTS 3,613,308 A * 10/1971 Klein et al. ..................... 47/17
4,091,566 A *  5/1978 Horvath et al. ................ 47/17

FOREIGN PATENT DOCUMENTS

DE    19522444 A1 *  1/1996
DE    19963029 A1 * 11/2000 ........... G01N 33/497

OTHER PUBLICATIONS

Steduto, P. e. a., "Water-Use Efficiency of Sweet sorghum Under Water Stress Conditions", Elsevier Science BV, Oct. 30, 1996, pp. 221-234.
Baker, Jeffrey T., e. a., "Canopy Gas Exchange Measurements of Cotton in an Open System", AJ Agronomy Journal, vol. 101, Issue 1, 2009, pp. 52-59.
Sun, Jindong, e. a., "FACE-ing the Global Change:Opportunities for Improvement in Phot0synthetic, Radiation Use Efficiency and Crop Yield", Elsevier Ireland Ltd., doi:10:1016/j.plantscie, BV, Jun. 8, 2009, pp. 511-522.
Zolnier, S., e. a., "Psychrometric and Ventilation Constraints for Vapor Pressure Deficit Control", Elsevier Science BV, as early as 2000, pp. 343-359.
Mu;;er, Johannes, e. a., "Through-Flow Chamber Co2/H2O Canopy Gas Exchange System-Construction, Microclimate, Errors, and Measurements in a Barley (*Hordeum vulgare* LI.) Field", Elsevier Science BV, as early as 2008, pp. 214-220.
Del Pilar Hernandez, Ana, e. a., "The Responses of Leaf Gas Exchange and Stomatal Conductance to Air Humidity in Shade-Growmn Coffe, Tea, and Cacao Plants as Compared With Sunflower", Rev. Bras. Fisiol. Vegetal, vol. 1, 1989, pp. 155-161.

* cited by examiner

*Primary Examiner* — Hezron E Williams
*Assistant Examiner* — Nathaniel Kolb
(74) *Attorney, Agent, or Firm* — C. W. Arnett; Faegre Baker Daniels, LLP

(57) ABSTRACT

A gas measurement system is provided that includes a mechanism for customizing gas supplied to the system. The system further includes a plurality of test locations that can be serviced by a common vessel portion and common sampling and testing infrastructure. The system further includes a controller that is able to control the customization of the supply gas and the location of the common vessel portion.

17 Claims, 2 Drawing Sheets

VARIABLE GAS SOURCE GAS EXCHANGE SYSTEM

PRIORITY

The present application claims priority to U.S. Provisional Application No. 61/505,399 filed Jul. 7, 2011, the disclosure of which is incorporated herein by reference.

FIELD

The present disclosure relates to a system for gas exchange chambers, and more particularly to method and system for a controlled source gas exchange chamber with automated testing capability.

BACKGROUND AND SUMMARY

Gas exchange chambers are used to monitor static states of plants and the composition of the immediately surrounding air once plants are allowed to exchange gasses with supplied ambient air.

According to an embodiment of the present disclosure, an open gas exchange measuring system is disclosed including: a controller; a test chamber; a customizable gas source that provides gas to the test chamber, the gas source being controlled by the controller, the controller providing for customizing characteristics of the gas provided to the test chamber as desired; and a measuring device.

According to another embodiment of the present disclosure, a gas measuring system is disclosed including: a controller; a gas source; a measuring device; a plurality of fixed lower test chamber portions, each lower test chamber portion having a position suitable for receiving a test subject, and a moveable upper test chamber portion. The moveable upper portion being sealable to each of the plurality of lower test chambers; the controller controlling the composition of gas supplied to upper test chamber portion from the gas source, the controller controlling the position of the moveable upper test chamber.

According to another embodiment of the present disclosure, a gas measuring system is provided including: a test chamber; a gas source; a first test chamber portion; a second test chamber portion; a third test chamber portion; and a controller including a data storage member. The data storage member including a plurality of instructions thereon that, when invoked by the controller, cause the system to perform the steps of: placing the second test chamber portion in contact with the first test chamber portion; customizing gas flow from the gas source to the first test chamber portion to provide a first gas to the first test chamber portion via the second test chamber portion, the first gas having a first set of desired customized characteristics; moving the second test chamber out of contact with the first test chamber portion and into contact with the third test chamber portion; and customizing gas flow from the gas source to the to the third test chamber portion to provide a second gas to the third test chamber portion via the second test chamber portion, the second gas having a second set of desired customized characteristics.

BRIEF DESCRIPTION OF THE DRAWINGS

The above-mentioned and other features of the disclosure, and the manner of attaining them, will become more apparent and the disclosure itself will be better understood by reference to the following description taken in conjunction with the accompanying drawings, wherein.

Corresponding reference characters indicate corresponding parts throughout the several views. The exemplifications set out herein illustrate exemplary embodiments of the invention, and such exemplifications are not to be construed as limiting the scope of the invention in any manner.

DETAILED DESCRIPTION

The embodiments disclosed herein are not intended to be exhaustive or to limit the disclosure to the precise forms disclosed in the following detailed description. Rather, the embodiments are chosen and described so that others skilled in the art may utilize their teachings.

Figure 1:
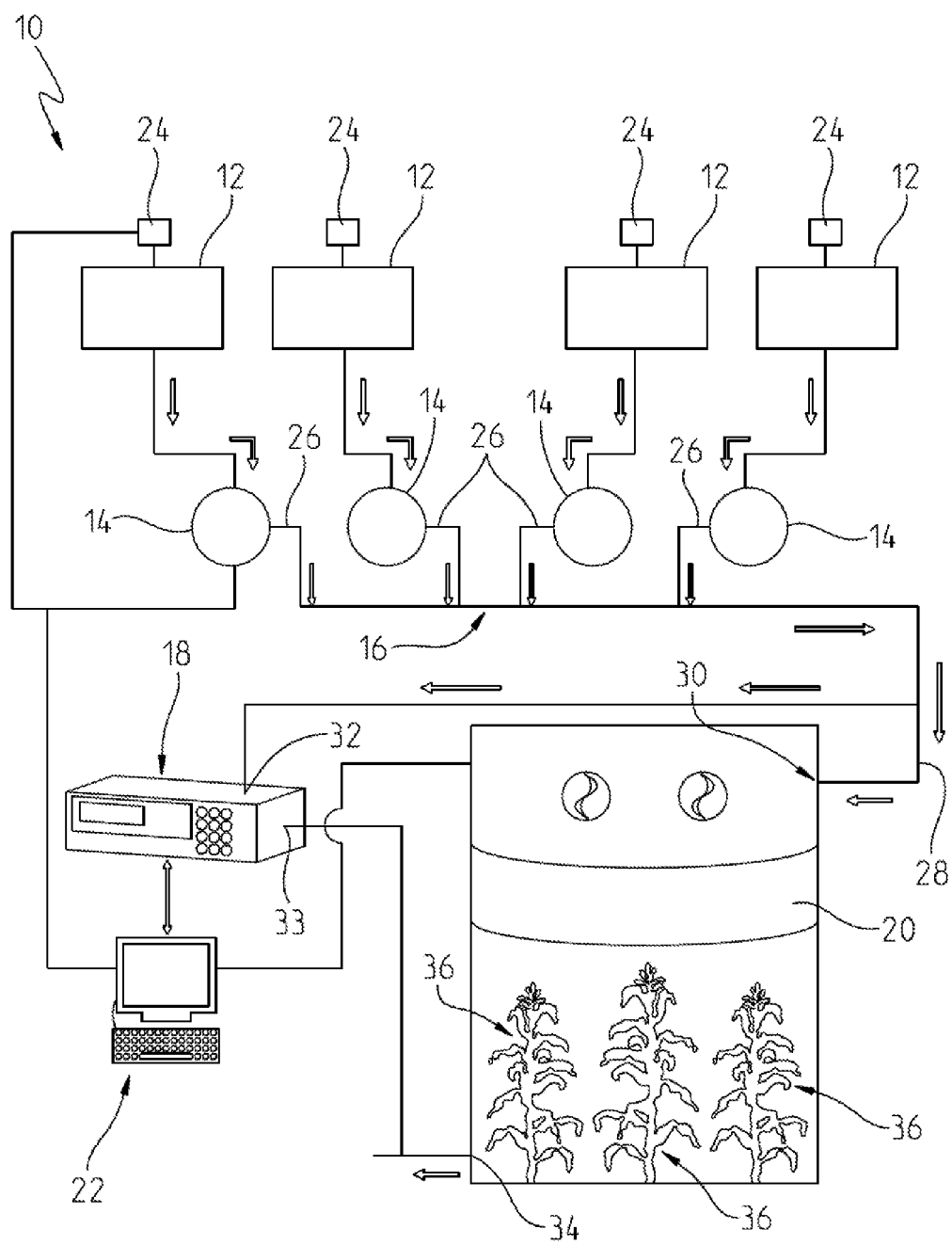
FIG. 1 illustrates a schematic of a system for supplying controlled gasses to one or more of a plurality of plants under test and for measuring gas exchange response.

Referring to FIG. 1, an exemplary gas exchange monitoring system 10 is shown. System 10 includes supply buffers 12, supply pumps 14, manifold 16, gas analyzer 18, chamber 20, and computer 22. System 10 is shown as an open system gas exchange chamber, however, it is envisioned that the concepts and teachings herein are also applicable to closed system gas exchange chambers.

Supply buffers 12 are gas repositories. Supply buffers 12 are provided with differing gaseous elements having differing physical/chemical characteristics. Buffers 12 are customizable according to tests desired to be carried out. By way of example, four buffers 12 are supplied with varying amounts of $CO_2$, $O_2$, ambient air, trace gasses (such as ethylene), or any other desired gaseous elements. Each buffer 12 is adjusted by temperature, vapor pressure deficit (VPD), and any other desired characteristic. To this end, heaters, coolers, humidifiers, dehumidifiers, and other condition altering devices 24 are coupled to each buffer 12.

Supply pumps 14 are coupled to each supply buffer 12. Supply pumps 14 control both the amount of gas supplied from each buffer 12, the flow rate of supplied gas, and in closed systems, the pressure at which the gas is supplied.

Supply pumps 14 supply gas from buffers 12 to manifold 16. Inputs 26 of manifold 16 are coupled to respective outputs of supply pumps 14. Manifold 16 combines the outputs from pumps 14. Manifold 16 further includes valves therein. Accordingly, system 10 is not restricted to supplying only the gaseous states of buffers 12, but rather combinations of the gaseous states of buffers 12 are achieved by varying the amounts of gas taken and mixed from each buffer 12. Outlet 28 of manifold 16 is supplied to inlet 30 of chamber 20 and to reference inlet 32 of gas analyzer 18.

Gas analyzer 18 is, in the present example, a $CO_2/H_2O$ analyzer, such as one produced by Li-Cor Biosciences with the model number of LI-7000. It should be appreciated that analyzer 18 is chosen to provide for monitoring of the chemicals/variables/features under study.

In addition to receiving input from manifold outlet 28, analyzer 18 receives input from outlet 34 of chamber 20 at sample inlet 33. Accordingly, analyzer 18 is provided with the gasses being supplied to chamber 20 and the gasses that result from the input gas being subjected to the presence of test subjects 36 (illustrated as plants) within chamber 20. Chamber outlet 34 is vented to ambient air in opens systems but could be vented to a collection chamber (not shown) or recirculated in other embodiments.

Computer 22 is coupled to analyzer 18 to allow monitoring, saving, and manipulation of the data provided by analyzer 18. As previously discussed, analyzer 18 includes at least two channels (from manifold outlet 28 and chamber outlet 34). Computer 22 includes programming to interface with analyzer 18 and allow graphical presentation of the data received therefrom. Computer 22 is further coupled to chamber 20, supply pumps 14, and manifold 16. Computer 22 is able to control supply pumps 14 and manifold 16 to provide desired gas compositions to chamber 20 at desired times.

Figure 2:
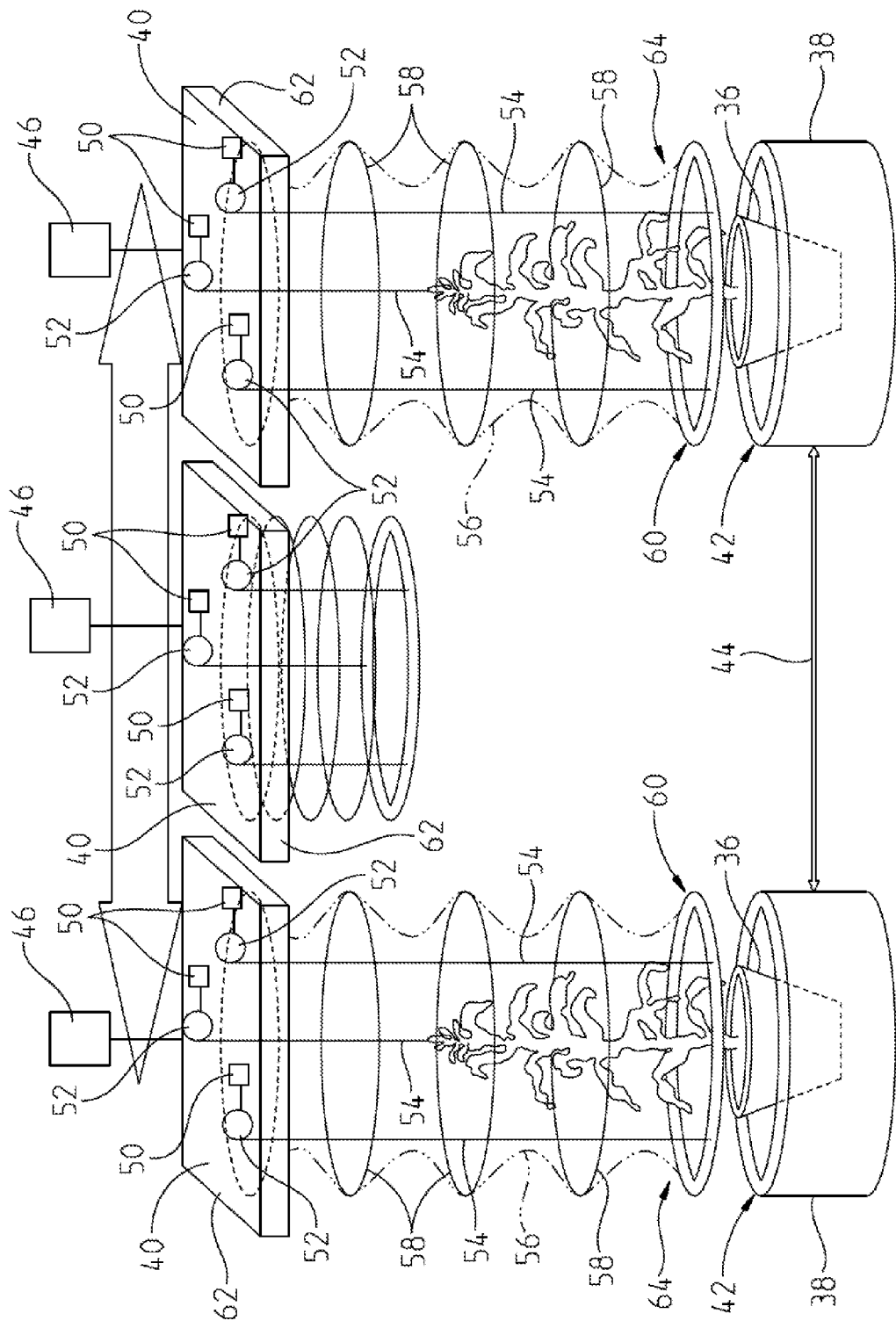
FIG. 2 illustrates a chamber usable in the system of FIG. 1.

Chamber 20 is shown in more detail in FIG. 2. Chamber 20 includes a fixed lower portion 38 and a moveable upper portion 40. Lower portion 38 is actually one of a plurality of identical lower portions 38. Moveable upper portion 40 is selectively associated with a plurality of lower portions 38. Embodiments are envisioned where system 10 also includes a plurality of upper portions 40. Test subjects 36 (or plants) under test are located within each lower portion 38.

Lower portions 38 are shown as being cylindrical and presenting an interface portion 42 on an upper lip. While other shapes and orientations are envisioned, lower portions within a system 10 are all similarly shaped and oriented. For example, another such orientation results in lower portions 38 being disposed within the floor or retractable into a floor such that interface portion 42 is flush with the floor. As shown, adjacent lower portions 38 are separated from each other by a defined inter-pot distance 44. The provided example provides that the inter-pot distance between lower portions 38 is constant for all lower portions 38. FIG. 2 shows two lower portions 38 that are separated in a left-right direction of the page. It should be appreciated that lower portions 38 are envisioned as being laid out in a grid of two dimensions (rows and columns), not shown. Accordingly, inter-pot distance 44 corresponds to a column width. The grid also has a row width that may or may not be equal to inter-pot distance 44 (column width). Embodiments are envisioned where the row width is equal to inter-pot distance 44. In the present example, inter-pot distance 44 is chosen such that the effect that tests being conducted at one lower portion 38 have minimal or no effect on tests being run at a second lower portion 38. Embodiments are also envisioned where inter-pot distance 44 is chosen to approximate the distance between plants that would be experienced in a planted field. Inter-pot distance 44 also allows for chamber 20 to fully enclose test subject 36 without enclosing any of adjacent test subject 36. Inter-pot distance 44 is also chosen to allow desired airflow once chamber 20 encloses test subject 36. Additionally, embodiments are envisioned wherein the floor of lower portion 38 includes a scale. The scale is coupled to computer 22 and provides an electronic weight signal thereto. Additionally, while chamber 20 is discussed as only enclosing one test subject 36 at a time, embodiments are envisioned where multiple test subjects 36 are enclosed together. In such embodiments, test subjects 36 enclosed together are usually of the same type.

Upper portion 40 includes base 62, movement linkages 46, input/output interfaces 48, motors 50, spools 52, cables 54, drape 56, support rings 58, and interface portion 60. Base 62 is shown as being a flat square member on which the balance of the pieces of upper portion 40 are mounted. However, it should be appreciated that the depiction of base 62 is conceptual. An actual base 62 is shaped and sized to support and provide mounting surfaces for the balance of the pieces of upper portion 40. Base 62 is coupled to movement linkages 46. Movement linkages 46 suspend upper portion 40 above lower portion 38 and test subjects 36. Movement linkages 46 further allow upper portion 40 to be moved and successively centered over multiple lower portions 38. Computer 20 is coupled to motors (not shown) that control the movement of movement linkages 46.

Base 62 provides an air-tight coupling to drape 56. Drape 56 is impervious to gas and illustratively made of a cylinder of flexible transparent plastic of a ply that can sustain repeated flexing. A plurality of support rings 58 is disposed on the interior of drape 56 at varying heights to maintain an internal opening diameter within drape 56. Alternatively, support rings 58 can take the form of a continual helix that approximates a spring.

Lower end 64 of drape 56 is coupled to interface portion 60. Interface portion 60 is sized to sealingly interface with interface portion 42 of lower portion 38. The seal of interface portion 42 to fixed lower portion 38 is air-tight to provide a volume within drape 56 that is gaseously isolated from the surrounding air.

Cables 54 are coupled to lower end 64 of drape and extend vertically upwardly to base 62. Cables 54 are further coupled to spools 52 that are coupled to and rotatable relative to base 62. Spools 52 are coupled to motors 50 that selectively turn spools to wind and unwind cables 54 from spools 52. Such winding and unwinding of cables 54 from spools 52 raise and lower, respectively, the interface portion 60 and drape 56. Accordingly, drape 56 is provided a lowered position where interface portion 60 seals to interface portion 42. Likewise, drape 56 is provided a raised position where interface portion 60 is disengaged from interface portion 42 and lower end 64 is raised to a height higher than the height of test subjects 36. The raised position of drape 56 causes/allows flexing of drape 56 to a compressed orientation.

Alternatively, embodiments are envisioned where harder plastic is used for drape 56. Such embodiments use the harder plastic in a telescoping manner such that collapsed (retracted) and expanded orientations are again provided. Air-tight seals are provided between telescoping portions to maintain the seal of chamber 20.

Input/output interfaces 48 are linked to chamber inlet 30 and chamber outlet 34, respectively. Input/output interfaces 48 are positioned on base 62 such that they are in communication with the interior volume of drape 56. Thus, when drape 56 is in its lowered position that defines an isolated volume, the isolated volume is in gaseous communication with manifold 16 and with gas analyzer 18. Inlet 30 is also envisioned to have specific ducting to provide that input gas is evenly distributed within chamber 20. Similarly, outlet 34 is positioned and ducted to maximize the likelihood that gas being sampled is gas that has interacted with test subjects 36 as opposed to coming directly from inlet 30.

In use, a location with an array containing a plurality of lower portions 38 is provided. Test subjects 36 are placed in one or more lower portions 38.

Computer 22 is provided with a plurality of data structures to control system 10 to conduct one or more experiments on test subjects 36. As noted, lower portions 38 are arranged with a set inter-pot distance 44. Regardless of the exact layout, computer 22 is provided data that indicates the positioning of the lower portions 38. The positioning data may be in the form of an existing data file or in the form of user input. Additionally, for any specific experiment run, computer 22 is provided data indicative of which lower portions 38 are in use (that contain a test subjects 36).

Computer 22 is likewise provided with data structures that contain instructions for movement linkages 46 (and the motors that control them) to cause moveable upper portion 40 to be positioned above each fixed lower portion 38.

Computer 22 accesses the data structure for the experiment protocol to determine which fixed lower portion 38 are in use for the protocol being executed. Similarly, the experiment protocol provides data indicative of what physical/chemical characteristics are provided by each of supply buffers 12. Computer 22 is provided with data structures that contain instructions for operation of supply pumps 14 and manifold 16 to cause desired gas compositions to be supplied to chamber 20.

Thus, with proper setup of lower portions 38 with test subjects 36 and of supply buffers 14, an experiment can be developed and carried out with a plurality of similar or different subjects (test subjects 36). Computer 22 is provided with a data structure that indicates the particular gas compositions to be supplied to each test subjects 36. Thus, for "n" test subjects 36, the experiment protocol provides a treatment to be carried out.

Once the experiment protocol data structure is invoked, computer 22 first positions moveable upper portion 40 over the first fixed lower portion 38 and test subjects 36 by emitting signals to instruct movement linkages 46 to move appropriately. Computer 22 then emits instructions to activate motors 50 and unspool cables 54 until interface portion 60 engages interface portion 42. Computer 22 then emits signals that selectively cause activation of supply pumps 14 and manifold 16 to produce the desired gaseous composition at inlet 30. As previously noted, the gaseous composition is likewise provided to gas analyzer 18. Accordingly, to the extent that the signals emitted from computer 22 do not produce an exactly precise gaseous composition, gas analyzer 18 is able to test the composition actually emitting from manifold 16.

Gas analyzer 18 is also testing the gas composition leaving chamber 20 via outlet 34. By taking successive readings, gas analyzer 18 is able to detect and report to computer 22 changes in gas composition over time. Differences in gas composition between inlet 30 and outlet 34 are presumed to be an artifact of the interaction between the provided gas and test subjects 36. Furthermore, in that the supplied gas is customizable, system 10 is able to measure the reactions/responses that plants have to changes in the provided atmosphere (gases). System 10 is further able to monitor transient reactions of test subjects 36 (and the resulting changes in output gasses) to the atmospheric changes. In one embodiment where system 10 monitors transient reactions, gas analyzer 18 focuses on readings between when the chamber is able to effect a full chamber air exchange and when the test subjects 36 are able to assume a new gas exchange equilibrium with the new gaseous composition. One such example is to focus on the times between 20 and 70 seconds after a new gas composition is provided to test subjects 36. In the embodiment, 20 seconds is relevant in that it is the time that the chamber needs to effect an air change within the chamber (3 exchanges per minute=1 change in 20 seconds). Additionally, 70 seconds is relevant in that test subjects 36 are believed to reach a gas exchange equilibrium 50 seconds after application of the new gaseous composition. Once the experiment is completed and the data is gathered, computer 22 emits signals to cause moveable upper portion 40 to move on to a second fixed lower portion 38 and test subjects 36.

To this end, drape 56 is retracted via motors 50, spools 52, and cables 54. Upper portion 40 is then moved above second fixed lower portion 38 and test subjects 36. Drape 56 is then lowered via motors 50, spools 52, and cables 54 such that interface portion 42 engages interface portion 60 of the second fixed lower portion 38. Again, computer 22 emits instructions to cause activation of supply pumps 14 and manifold 16 to produce the desired gaseous composition at inlet 30. It should be appreciated that the gas composition supplied to the second fixed lower portion 38 can be the same or different than the gas composition supplied to the first fixed lower portion 38.

Additionally, the gas composition can be changed in the midst of a trial (i.e. the trial may be testing the plant response to going from a first gas composition to a second gas composition). Such gas composition changes include but are not limited to increases/decreases in atmospheric vapor pressure deficit (VPD), temperature, $CO_2$ concentration, and consecutive changes (raising or lowering) these variables. Furthermore, monitoring output changes relative to the input changes provide transient reaction data. The transient reaction data can provide information about the performance of the test subjects 36 in terms of change in canopy gas exchange capacity, instantaneous water use efficiency in reaction to environmental stimulus, and traits such as drought tolerance, nitrogen use efficiency, tolerance to flood stress, photosynthetic capacity, and any others desired and detectable via the described devices and methods. Additional properties, such as canopy transpiration, transpiration rate, net $CO_2$ assimilation, $CO_2$ assimilation rate, net $CO_2$ assimilation rate, $CO_2$ concentration, Irradiance, Leaf Stomatal Conductance, and leaf Surface Temperature can also be determined. Accordingly, system 10 provides a high throughput system for screening for traits such as, but not limited to, drought tolerance and nitrogen use efficiency.

While this invention has been described as having preferred designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this disclosure pertains and which fall within the limits of the appended claims.

The invention claimed is:

1. An open gas exchange measuring system including:
    a controller;
    a test chamber including a movable upper portion that selectively engages a first lower portion wherein a motor is coupled to the upper portion such that the upper portion is movable between the first lower portion and a second lower portion;
    a customizable gas source that provides gas to the test chamber, the gas source being controlled by the controller, the controller providing for customizing characteristics of the gas provided to the test chamber; and
    a gas measuring device.

2. The system of claim 1, wherein the customizable gas source includes a plurality of gas sources, the controller causing gas from one or more of the plurality of gas sources to be mixed to provide customized characteristics in gas supplied to the test chamber.

3. The system of claim 1, further including an exhaust port that fluidly links the test chamber to ambient air.

4. The system of claim 3, wherein the exhaust port is permanently open.

5. The system of claim 1, wherein the upper portion includes a drape that provides a barrier to airflow.

6. The system of claim 1, wherein the customizable gas source provides the sole gas input the test chamber.

7. A gas measuring system including:
    a controller;
    a gas source;
    a gas measuring device;
    a plurality of fixed lower test chamber portions, each lower test chamber portion having a position suitable for receiving a test subject, and
    a moveable upper test chamber portion, the moveable upper portion being coupleable to each of the plurality of lower test chambers; the controller controlling the composition of gas supplied to upper test chamber portion from the gas source, the controller controlling the position of the moveable upper test chamber.

8. The system of claim 7, wherein the upper test chamber portion has a retracted position and an expanded position, transition from the retracted position to the expanded position including coupling a portion of the upper test chamber portion to a coupling portion of the lower test chamber portion.

9. The system of claim 7, wherein the upper test chamber portion includes a drape that impedes airflow.

10. The system of claim 7, wherein positions of the plurality of fixed lower test chamber portions are known by the controller.

11. The system of claim 7, wherein the controller includes software that positions the moveable upper test chamber portion to align with one of the plurality of fixed lower test chamber portions.

12. The system of claim 7, wherein the gas source includes a plurality of different gasses and the controller is operable to control the mixture of the plurality of different gasses to be provided to the moveable upper test chamber portion.

13. A gas measuring system including:
a test chamber;
a gas source;
a first test chamber portion;
a second test chamber portion;
a third test chamber portion;
a gas measuring device; and
a controller including a data storage member, the data storage member including a plurality of instructions thereon that, when invoked by the controller, cause the system to perform the steps of:
placing the second test chamber portion in contact with the first test chamber portion;
customizing gas flow from the gas source to the first test chamber portion to provide a first gas to the first test chamber portion via the second test chamber portion, the first gas having a first set of desired customized characteristics;
moving the second test chamber out of contact with the first test chamber portion and into contact with the third test chamber portion; and
customizing gas flow from the gas source to the to the third test chamber portion to provide a second gas to the third test chamber portion via the second test chamber portion, the second gas having a second set of desired customized characteristics.

14. The system of claim 13, wherein the second test chamber portion includes a drape that impedes airflow.

15. The system of claim 13, wherein the gas source is the sole source of gas supplied to the second test chamber portion.

16. The system of claim 13, wherein the system is operable to supply gas to a plurality of plants.

17. The system of claim 13, wherein the customized characteristics of the first and second gasses are selected from the group including chemical makeup, temperature, and vapor pressure deficit.

* * * * *